US012736536B2

(12) United States Patent
Yazawa et al.

(10) Patent No.: US 12,736,536 B2
(45) Date of Patent: Sep. 15, 2026

(54) CANCER BIOMARKER IN PANCREATIC CANCER OR MALIGNANT INTRADUCTAL PAPILLARY MUCINOUS NEOPLASM

(71) Applicant: NATIONAL UNIVERSITY CORPORATION GUNMA UNIVERSITY, Gunma (JP)

(72) Inventors: Shin Yazawa, Gunma (JP); Norio Kubo, Gunma (JP); Ken Shirabe, Gunma (JP)

(73) Assignee: NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 715 days.

(21) Appl. No.: 18/018,121

(22) PCT Filed: Jul. 26, 2021

(86) PCT No.: PCT/JP2021/027546
§ 371 (c)(1),
(2) Date: Jan. 26, 2023

(87) PCT Pub. No.: WO2022/024995
PCT Pub. Date: Feb. 3, 2022

(65) Prior Publication Data

US 2023/0280347 A1 Sep. 7, 2023

(30) Foreign Application Priority Data

Jul. 27, 2020 (JP) ................................ 2020-126547

(51) Int. Cl.
*G01N 33/53* (2006.01)
*G01N 33/543* (2006.01)
*G01N 33/57525* (2026.01)

(52) U.S. Cl.
CPC ..... *G01N 33/57525* (2026.01); *G01N 33/543* (2013.01); *G01N 2333/4724* (2013.01); *G01N 2333/4728* (2013.01); *G01N 2470/04* (2021.08)

(58) Field of Classification Search
None
See application file for complete search history.

(56) References Cited

U.S. PATENT DOCUMENTS

2007/0178538 A1 8/2007 Haab
2011/0020941 A1 1/2011 Rudd et al.
2019/0004050 A1 1/2019 McConnell et al.

FOREIGN PATENT DOCUMENTS

JP 2010-540953 12/2010
JP 2019-11978 1/2019
JP 2019-500609 1/2019
WO 2014/136301 9/2014

OTHER PUBLICATIONS

Balmana et al., Increased a1-3 fucosylation of a-1-acid glycoprotein (AGP) in pancreatic cancer, Journal of Porteomics 132, 2016, pp. 144-154). (Year: 2016).*
International Search Report issued Sep. 21, 2021 in International (PCT) Application No. PCT/JP2021/027546.
Balmaña, Meritxell et al., "Increased α1-3 fucosylation of α-1-acid glycoprotein (AGP) in pancreatic cancer", Journal of Proteomics, 2016, vol. 132, pp. 144-154.
Hashimoto, Shinji et al., "$\alpha_1$-Acid Glycoprotein Fucosylation as a Marker of Carcinoma Progression and Prognosis", Cancer, Dec. 2004, vol. 101, No. 12, pp. 2825-2836.
Yazawa, Shin et al., "Fucosylated Glycans in al-Acid Glycoprotein for Monitoring Treatment Outcomes and Prognosis of Cancer Patients", PLOS One, Jun. 2016, vol. 11(6):e0156277, 20 pages.
Tsukagoshi, Mariko et al., "Evaluation of the International Consensus Guidelines for the Surgical Resection of Intraductal Papillary Mucinous Neoplasms", Dig Dis Sci, 2018, vol. 63, pp. 860-867.
Amemiya, Haley M. et al., "The ENCODE Blacklist: Identification of Problematic Regions of the Genome", Scientific Reports, 2019, vol. 9:9354, 5 pages.
Asao, Takayuki et al., "Development of a Novel System for Mass Spectrometric Analysis of Cancer-Associated Fucosylation in Plasma α1-Acid Glycoprotein", BioMed Research International, 2013, vol. 2013, Article ID 834790, 9 pages.
Yazawa, Shin et al., "The Presence of CA19-9 in Serum and Saliva from Lewis Blood-group Negative Cancer Patients", Jpn. J. Cancer Res., 1988, vol. 79, pp. 538-543.
Yazawa, Shin et al., "Genetic and Enzymatic Evidence for Lewis Enzyme Expression in Lewis-negative Cancer Patients", Cancer Research, Apr. 1995, vol. 55, pp. 1473-1478.
Yazawa, Shin et al., "A new enzyme immunoassay for the determination of highly sialylated and fucosy lated human α1-acid glycoprotein as a biomarker of tumorigenesis", Clinica Chimica Acta, 2018, 478:120-128.

* cited by examiner

*Primary Examiner* — Gary Counts
(74) *Attorney, Agent, or Firm* — Wenderoth, Lind & Ponack, L.L.P.

(57) ABSTRACT

Fucosylated $\alpha_1$-acid glycoprotein (fAGP) was found to be useful for the diagnosis of pancreatic cancer and malignant intraductal papillary mucinous neoplasm (IPMC), resulting in the finding of a new biomarker for pancreatic cancer or malignant intraductal papillary mucinous neoplasm (IPMC), in particular, a new biomarker useful for rapid diagnosis of malignant intraductal papillary mucinous neoplasm (IPMC) that increases the accuracy of malignant intraductal papillary mucinous neoplasm (IPMC) and aids conventional imaging diagnosis by making a suitable preoperative diagnosis of a benign neoplasm or a malignant neoplasm in intraductal papillary mucinous neoplasm (IPMN).

4 Claims, 1 Drawing Sheet

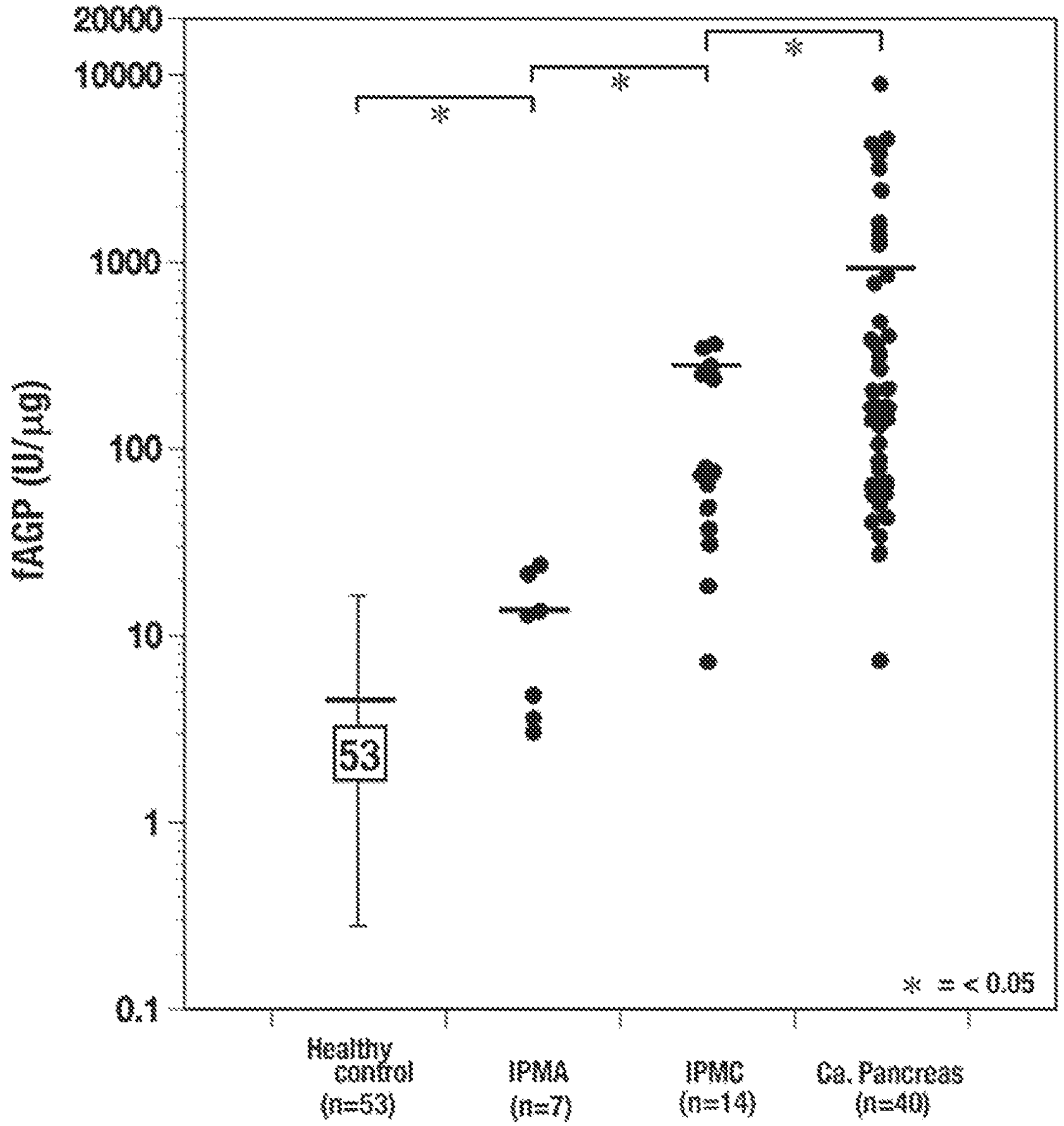
20000
10000
1000
100
10
1
0.1
fAGP (U/μg)
53
※
※ = < 0.05
Healthy control (n=53)
IPMA (n=7)
IPMC (n=14)
Ca. Pancreas (n=40)

CANCER BIOMARKER IN PANCREATIC CANCER OR MALIGNANT INTRADUCTAL PAPILLARY MUCINOUS NEOPLASM

TECHNICAL FIELD

The present invention relates to a novel cancer biomarker in pancreatic cancer or malignant intraductal papillary mucinous neoplasm.

BACKGROUND OF THE INVENTION

Pancreatic cancer is the second most common cause of death in Japan after lung cancer, stomach cancer, and colorectal cancer, and while the number of deaths has been declining in many cancers in recent years, the mortality rate of pancreatic cancer is increasing. Therefore, development of a novel biomarker that enables early diagnosis as well as a new treatment method is strongly desired.

On the other hand, intraductal papillary mucinous neoplasm (hereinafter, also referred to as IPMN) is the most common cystic neoplasm in pancreas, and is a disease that may turn cancerous. In IPMNs, it is known that they progress from adenomas (benign IPMNs, hereafter, also referred to as IPMA) to carcinomas (malignant IPMNs, hereafter, also referred to as IPMC). Although diagnosing IPMNs has become relatively easy with the development of testing methods, problems remain regarding resection of lesions as the basis of treatment. Specifically, IPMN patients are usually examined for carcinogenic risk based on each imaging finding in accordance with the IPMN International Consensus Guidelines to determine the indication for surgery, which may include IPMA that is not originally indicated for surgery, as well as IPMC that has turned cancerous, and the accuracy is reported to be 64.3% (see Non-Patent Document 1).

Furthermore, preoperative serodiagnosis by cancer markers targeting pancreatic cancer, which has been used conventionally, has been difficult to apply to diagnosis due to the low positive rate of the marker. Therefore, considering the risks associated with pancreatectomy, it has been an urgent need to establish a new biomarker that is useful for early diagnosis of progression to malignancy in IPMN and for improving the accuracy of IPMC.

$\alpha_1$-Acid glycoprotein (hereinafter, also referred to as AGP) is an inflammatory marker whose concentration in blood increases during inflammation, and the present inventors have elucidated a cancerous change occurred in glycans of the AGP molecule, and revealed that a quantitative changes in fucosylated AGP (hereinafter, also referred to as fAGP) is useful not only for diagnosis of the presence of malignant tumors but also for elucidation of prognostic prediction and therapeutic effects (Patent Document 1, Non-Patent Document 2). Furthermore, the present inventors have also revealed the possibility of early detection of recurrence and metastasis in a variety of chemotherapy cases (Non-Patent Document 3), as well as the possibility of applying immunotherapy, which has recently achieved a groundbreaking therapeutic effect, to determine the effectiveness of the treatment (Non-Patent Document 4).

CITATION LIST

Patent Documents

Patent Document 1: JP 2019-11978 A

Non-Patent Documents

Non-Patent Document 1: Dig. Dis. Sci., 63:860-867, 2018

Non-Patent Document 2: Cancer, 101:2825-2836, 2004

Non-Patent Document 3: PLOS ONE, 11 (6) e0156277, 2016

Non-Patent Document 4: Sci. Reports, doi.org: 10.1038, 2019

Non-Patent Document 5: BioMed. Res. Inter., Vol 2013, Article ID 834790, 2013

Non-Patent Document 6: Clinica Chimica Acta, 478:120-128, 2018

Non-Patent Document 7: Jpn. J. Cancer Res. (Gann), 79:538-543, 1988

Non-Patent Document 8: Cancer Res., 55:1473-1478, 1995

SUMMARY OF INVENTION

Technical Problem

An object is to provide a new biomarker for pancreatic cancer or IPMC, in particular, a new biomarker useful for rapid diagnosis of IPMC that increases the accuracy of IPMC and aids conventional imaging diagnosis by making a suitable preoperative diagnosis of a benign neoplasm or a malignant neoplasm in IPMN.

Solution to Problem

The present inventors diligently studied to solve the above-described problems and found that fAGP is a useful biomarker for the diagnosis of pancreatic cancer or IPMC, thereby arriving at the present invention.

In other words, the present invention is as follows.

[1] A method of acquiring data for diagnosing pancreatic cancer or malignant intraductal papillary mucinous neoplasm (IPMC), comprising measuring the amount of fucosylated $\alpha_1$-acid glycoprotein (fAGP) in a specimen.

[2] The method according to [1], wherein the specimen is a plasma or a serum.

[3] The method according to [1] or [2], wherein
the amount of fucosyl residues in $\alpha_1$-acid glycoprotein (AGP) is measured, and said method comprises:
a step of desialylating AGP in a specimen; and
a step of measuring the amount of fucosyl residues by an enzyme immunoassay (EIA) using an anti-AGP antibody that is immobilized on a substrate and whose sugar chain has been defucosylated, and a lectin that recognizes fucosyl residues in the desialylated AGP.

[4] The method according to [3], wherein the desialylation is performed by a sialidase treatment, and the defucosylation is performed by periodate oxidation.

[5] The method according to [3] or [4], wherein the lectin is *Aleuria aurantia* lectin (AAL).

[6] The method according to any one of [3] to [5], further comprising the following steps:
a step of quantifying AGP in the specimen; and
a step of normalizing the amount of the fucosyl residues by the amount of AGP.

[7] The method according to any one of [1] to [6], wherein the diagnosis is based on a criterion that a pancreatic cancer or malignant intraductal papillary mucinous neoplasm (IPMC) is present when the amount of fAGP in a specimen is greater than a reference value or the amount of fAGP in a specimen collected from a healthy subject or a patient with a benign intraductal papillary mucinous neoplasm (IPMA).

[8] The method according to any one of [1] to [7], wherein the diagnosis is a diagnosis of a prognosis of a cancer treatment.

[9] A kit for diagnosing pancreatic cancer or malignant intraductal papillary mucinous neoplasm (IPMC), the kit comprising:

(A) a reagent for desialylation;

(B) a substrate for an EIA on which an anti-AGP antibody is immobilized; and (C) a reagent for defucosylation of an anti-AGP antibody immobilized on a substrate for an EIA.

[10] The kit according to [9], further comprising (D) a labeled lectin and/or (E) an avidin-labeled enzyme.

[11] The kit according to [9] or [10], further comprising:

(F) a substrate for sandwich ELISA on which an anti-AGP antibody is immobilized for quantifying AGP in a specimen; and (G) a solution containing an enzyme-labeled anti-AGP antibody.

Advantageous Effects of Invention

According to the present invention, by measuring the amount of fAGP in a specimen, a novel biomarker useful for diagnosing pancreatic cancer or IPMC can be provided. By using such a biomarker as an indicator, IPMC can be distinguished from IPMA, and such a biomarker is also useful in predicting a prognosis of IPMN.

BRIEF DESCRIPTION OF DRAWINGS

FIG. 1 illustrates measurement results of the amount of fAGP in serum samples from pateints with IPMN and other pancreatic cancers. Each horizontal line in the FIGURE represents the mean value of each group.

DESCRIPTION OF EMBODIMENTS

One embodiment of the present invention is a data acquisition method for diagnosing pancreatic cancer or IPMC, comprising measuring the amount of fAGP in a specimen.

The data acquisition method of the present embodiment is intended to assist in the diagnosis of pancreatic cancer or IPMC. The present method is useful for distinguishing IPMC from IPMA and is useful for predicting a prognosis of IPMN, especially for diagnosing the occurrence of pancreatic cancer in IPMN. In the present invention, IPMC, a malignant neoplasm, may be categorized as pancreatic cancer, while IPMA, a benign neoplasm, is not categorized as pancreatic cancer.

An animal from which a specimen is derived is preferably a mammal, such as a human or rat, and a human is more preferable. As a specimen, a body fluid derived from humans is preferable, and examples thereof include a blood, a lymph fluid, a spinal fluid, a urine, and an ascites fluid. A specimen can be collected or stored according to a conventional method. In the case of a blood, a plasma or a serum is preferably used, and preparation or storage thereof can be done according to a conventional method.

The present invention may include a step of collecting a specimen from an animal to be diagnosed.

Measurement of the amount of fAGP is not particularly restricted, and can be performed by measuring the amount of fucosyl residues in AGP. For example, measurement may be performed based on the method described in Patent Document 1 as described below, and according to this method, the amount of fAGP can be calculated easily and from a very small amount of a serum sample (for example, 1 drop, 25 μl).

[Process of Desialylating AGP in Specimen]

The measurement method may include a step of desialylating AGP in a specimen. When sugar chains of AGP in a specimen remain highly sialylated, capture of AGP by anti-AGP antibody and detection of fucosyl residues by lectin in an EIA are inhibited.

(Desialylation)

Desialylation is not particularly restricted as long as such desialylation can release sialyl residues attached to non reducing ends of sugar chains expressed on the AGP molecule through α2,3 and α2,6 linkages. Desialylation is preferably performed using a desialylating enzyme, such as a sialidase (also known as a neuraminidase).

The sialidase is not particularly restricted as long as such a sialidase is an exo-type having specificity for the α2,3 and α2,6 sialyl linkages present at a non-reducing end in an AGP sugar chain. Sialidases derived from a variety of organisms can also be used. Sialidases may be used singly, or two or more kinds thereof may be used in combination, and a sialidase derived from *Arthrobacter ureafaciens*, which efficiently hydrolyzes both sialyl linkages, is preferably used.

The amount of a sialidase used in a desialylation treatment with a sialidase is not particularly limited as long as sufficient sialyl residues are released from a non-reducing end of the sugar chain, and the amount per 1 μg of AGP is preferably 0.005 mU or more, more preferably 0.01 mU or more, and further preferably 0.02 mU or more. On the other hand, the amount is preferably 2 mU or less, more preferably 1.5 mU or less, and further preferably 1 mU or less.

The amount of enzyme required to degrade 1 μmol of sialic acid per minute at a pH of 5.0 and 37° C. using sialyllactose as a substrate is defined as 1 U (unit).

The treatment time for desialylation with a sialidase is not particularly limited as long as sufficient sialyl residues are released from the non-reducing end of a sugar chain, and is preferably 20 minutes or longer, more preferably 30 minutes or longer, and further preferably 1 hour or longer. On the other hand, the upper limit is not particularly restricted, and may be, for example, 2 hours or less.

The treatment temperature in desialylation by a sialidase is not particularly restricted as long as sufficient sialyl residues are released from the non-reducing end of a sugar chain, and is preferably room temperature (for example, 25° C.) or higher, more preferably 30° C. or higher, and further preferably 35° C. or higher. On the other hand, the upper limit is a temperature at which a sialidase remains active, and is preferably 38° C. or lower, and particularly preferably 37° C.

As a buffer solution for desialylation by a sialidase, a common buffer in the case of using a biochemical method can be used. Examples of the buffer solution include an acetate buffer, a phosphate buffer, a citrate buffer, a borate buffer, a tartrate buffer, and a phosphate buffered saline (PBS). Regarding the concentration of a buffer solution, a common concentration in the case of using a biochemical method can be used.

The pH of a buffer solution is not particularly restricted as long as desialylation proceeds, and is preferably 6.0 or higher, more preferably 6.5 or higher, and further preferably 6.8 or higher. On the other hand, the pH is preferably 8.0 or less, more preferably 7.5 or less, and further preferably 7.2 or less.

After desialylation by a sialidase, the sialidase is preferably inactivated. Inactivation can be done according to a conventional method. Examples of the method include a treatment at 90° C. for 5 minutes in a dilution of 490 μl of PBS per 10 μl of a serum.

Specifically, a desialylation step may include a step of mixing a specimen and a sialidase, a step of treating a mixed solution of the specimen and the sialidase at a temperature at which the sialidase remains active for a desired period of time, and a step of inactivating the sialidase.

[Process of Measuring Amount of Fucosyl Residues by EIA]

The measurement method includes, after the above-described step of desialylating AGP in a specimen, a step of measuring the amount of fucosyl residues by an enzyme immunoassay (EIA) using an anti-AGP antibody that is immobilized on a substrate and whose sugar chain is defucosylated, and a lectin that recognizes fucosyl residues expressed on desialylated AGP. By reacting AGP with an anti-AGP antibody in which a sugar chain on a substrate has been defucosylated after a step of desialylating AGP, more AGPs containing a variety of fucosyl residues in a specimen can be measured compared with the case of reacting with an anti-AGP antibody in which a sugar chain on a substrate have been defucosylated prior to the step of desialylating AGP.

The present step may include, for example, a step of defucosylating the sugar chain of an anti-AGP antibody; a step of immobilizing the anti-AGP antibody whose sugar chain is defucosylated on a substrate; a step of binding an anti-AGP antibody whose sugar chain is defucosylated immobilized on the substrate to AGP in a specimen by adding the specimen to the substrate; a step of binding a lectin that recognizes the fucosyl residue of AGP captured by anti-AGP antibody; and a step of measuring the amount of the fucosyl residues by measuring a lectin by an EIA.

In the present step, an anti-AGP antibody immobilized on a substrate used in the EIA is one whose sugar chain is defucosylated.

When a sugar chain of an anti-AGP antibody (Fc region) remains fucosylated, the above-described lectin that recognizes fucosyl residues of desialylated AGP binds not only to the fucosyl residues of the AGP but also to fucosyl resideus of the anti-AGP antibody immobilized on the substrate when an EIA is performed, and the amount of the fucosyl residue of the AGP cannot be accurately measured.

Examples of the substrate include a well provided in a plate and a bead. The anti-AGP antibody that is immobilized on a substrate whose sugar chain is defucosylated used for an EIA may be one which is defucosylated on the substrate after the anti-AGP antibody is immobilized on the substrate before defucosylation, or one whose sugar chain is defucosylated in advance at the stage of immobilization on the substrate. The method for immobilizing an anti-AGP antibody on a substrate, whether the antibody is an anti-AGP antibody before defucosylation or an anti-AGP antibody whose sugar chain is defucosylated in advance, can be a method used in a conventional EIA.

(Defucosylation)

When defucosylation is performed on an anti-AGP antibody before defucosylation that is immobilized on a substrate for an EIA, the method is not particularly restricted, and is preferably performed by a treatment using a solution for defucosylation, such as periodate oxidation using a sodium periodate solution.

When periodic acid is used, the concentration is not particularly restricted as long as sufficient defucosylation is achieved, and is preferably 5 mM or higher, more preferably 7 mM or higher, and further preferably 8 mM or higher. On the other hand, the concentration is preferably 20 mM or less, more preferably 15 mM or less, and further preferably 12 mM or less.

The treatment time for defucosylation using periodic acid is not particularly restricted as long as sufficient defucosylation is achieved, and is preferably 20 minutes or longer, more preferably 30 minutes or longer, and further preferably 50 minutes or longer. On the other hand, the upper limit is preferably 2 hours or less in order to keep damage caused by a defucosylation treatment to an antibody used at a low level.

The treatment temperature for defucosylation using periodic acid is not particularly restricted as long as sufficient defucosylation is achieved, and is preferably 15° C. or higher, more preferably 20° C. or higher, and further preferably 25° C. or higher. On the other hand, the treatment temperature is preferably 40° C. or less, more preferably 35° C. or less, and further preferably 30° C. or less.

When periodic acid is used, a commonly used buffer solution when using a biochemical method can be used. Examples of the buffer solution include an acetate buffer solution, a phosphate buffer solution, a citrate buffer solution, a borate buffer solution, a tartrate buffer solution, a tris buffer solution, and a phosphate-buffered saline solution (PBS). Such a buffer solution may contain a surfactant such as TWEEN® 20 or TWEEN® 80, if appropriate. Regarding the concentrations of a buffer solution and a surfactant, general concentrations when using a biochemical method can be used.

The pH of a buffer solution is not particularly restricted as long as defucosylation proceeds, and is preferably 6.0 or higher, more preferably 6.5 or higher, and further preferably 6.8 or higher. On the other hand, the pH is preferably 8.0 or less, more preferably 7.5 or less, and further preferably 7.2 or less.

Defucosylation using periodic acid is preferably performed under light shielding. After defucosylation using periodic acid, a substrate can be prepared in the same manner as in a conventional EIA, such as washing the substrate with a buffer solution, warming the substrate in PBS containing 1% BSA at room temperature for 2 hours or at 4° C. overnight, washing with a washing buffer (for example, PBS containing 0.05% TWEEN® 20), and then performing an EIA.

In general, the activity of an antibody may be protected by performing a reduction treatment after defucosylation with periodic acid, and since there is no significant difference in results of the quantification of fucosyl residues in AGP with or without a reduction treatment in the measurement method of the present invention, it is preferable not to include a reduction treatment step after defucosylation.

The step of defucosylating a sugar chain of an anti-AGP antibody may include: a step of bringing a solution for defucosylation into contact with the anti-AGP antibody on a substrate after immobilizing the anti-AGP antibody on the substrate; a step of treating the sugar chain of the anti-AGP antibody immobilized on the substrate at a desired temperature for a desired time to defucosylate the sugar chain of the anti-AGP antibody on the substrate; and a step of washing the substrate.

The step of immobilizing an anti-AGP antibody whose sugar chain is defucosylated on a substrate can be performed by a method known to those skilled in the art, and may include: a step of bringing the substrate into contact with the anti-AGP antibody; a step of treatment at a desired temperature and for a desired time to immobilize the anti-AGP antibody on the substrate; and a step of washing the substrate.

A step of adding a specimen to a substrate to bind an anti-AGP antibody whose sugar chain is defucosylated immobilized on this substrate to AGP of the specimen is not particularly limited as long as an antigen-antibody reaction between AGP and anti-AGP is sufficiently carried out, and can be carried out for a desired period of time and at a desired temperature.

A step of binding a lectin that recognizes fucosyl residues in AGP captured by an anti-AGP antibody is not particularly limited as long as the lectin can recognize the fucosyl residue on the AGP, and can be carried out for a desired period of time and at a desired temperature. The step may include a step of biotin-labeling of lectin in advance.

(Lectin Recognizing Fucosyl Residues in Desialylated AGP)

The lectin may be any one that binds to Fuc$\alpha$1,3GlcNAc linkages present on an AGP sugar chain, and is preferably an *Aleuria aurantia* lectin (AAL). These may be natural or artificially produced. A lectin may be a recombinant protein having high homology to natural AAL, and high homology means, for example, 80% or more homology. The AAL may be labeled or modified as used in a conventional EIA.

(Detection)

As a method for detecting binding of a lectin that recognizes fucosyl residues in desialylated AGP to AGP by recognizing the fucosyl reidues, a conventional EIA can be used. A lectin itself may be labeled, or, for example, a lectin may be biotin-labeled in advance, and after binding fucosl resideus of AGP to the biotin-labeled lectin, an avidin-labeled enzyme may be bound, and a reaction of the enzyme may be detected using color development or emission.

For the above-described enzyme, in all cases, a common enzyme used in a conventional EIA can be used. Examples of the enzyme include horseradish peroxidase (HRP) and alkaline phosphatase (ALP).

The substrate can be any substrate that corresponds to an enzyme to be used, and examples of a substrate for HRP include 3,3',5,5'-tetramethylbenzidine (TMB) or 2,2'-azino-bis [3-ethylbenzothiazoline-6-sulfonic acid]-diammonium salt (ABTS), and o-phenylenediamine dihydrochloride (OPD). Examples of a substrate for ALP include para-nitrophenyl phosphoric acid (PNPP).

(EIA)

The EIA in the present step can be carried out in the same manner as a conventional method. In addition to the reaction temperature and the reaction time, the type of reagent, the concentration of reagent, and the detection method of fluorescence or color development can all comply with a conventional method.

As an example, a case in which a lectin that recognizes and binds to the fucosyl residue of desialylated AGP is used as biotin-labeled AAL, and the binding is detected by adding avidin-labeled enzyme HRP and coloration against substrate TMB will be described.

First, as described above, a substrate for EIA on which an anti-AGP antibody defucosylated by periodate oxidation is immobilized is prepared. In order to prevent non-specific adsorption to a substrate, blocking may be performed by a buffer solution for blocking which is used in a conventional method, such as PBS containing 10% sorbitol plus 1% BlockAce or PBS containing 2% bovine serum albumin (BSA), preferably PBS containing 10% sorbitol plus 1% BlockAce.

Next, a sample containing desialylated AGP is used to bind a defucosylated anti-AGP antibody, which is immobilized on a substrate and the desialylated AGP, and then the unbound component is removed by washing with a washing buffer (for example, PBS containing 0.05% TWEEN® 20).

Next, a biotin-labeled AAL is used to bind the fucosyl residue in desialylated AGP captured by the anti-AGP antibody to the biotin-labeled AAL, and the unbound biotin-labeled AAL is removed by washing with a washing buffer. BlockAce-free PBS can be used to adjust the concentration of biotin-labeled AAL, and 0.4% BlockAce-added PBS can be used to adjust the concentration of another antibody.

Next, the biotin-labeled AAL is bound to an avidin-labeled enzyme HRP using an avidin-labeled enzyme HRP, and the unbound avidin-labeled enzyme HRP is removed by washing with a washing buffer.

Next, a substrate TMB of the enzyme HRP is added, and the color development is detected in the same manner as in a conventional antibody-lectin EIA.

The measurement method of the present invention preferably further includes a step of converting the amount of fucosylated AGP from the above-described color development amount.

Examples of a method used in the present step include a method of converting the amount of fucosylated AGP in a specimen using a calibration curve from the color development amount or emission amount measured by the above-described EIA.

A calibration curve is preferably prepared, for example, from the relationship between the amount of fucosylated AGP obtained by desialylation of a highly fucosylated AGP obtained from a serum or an ascites by the method described in Non-Patent Document 5 and a similar EIA and the color development amount or the emission amount (U/ml).

A step of associating the amount of fucosyl residue in an $\alpha_1$-acid glycoprotein (AGP) in a specimen thus obtained or the amount of converted fucosylated AGP as an indicator of pancreatic cancer or malignant intraductal papillary mucinous neoplasm (IPMC) may be included.

The measurement method preferably further includes: a step of quantifying AGP in the above-described specimen; and a step of normalizing the amount of a fucosyl sugar chain by the above-described amount of AGP.

[Process of Quantifying AGP in Specimen]

The measurement method preferably includes a step of quantifying AGP in a specimen.

The method of quantifying AGP in a specimen is not limited, and examples thereof include a method of performing a sandwich ELISA using an anti-AGP antibody immobilized on a substrate and an enzyme-labeled anti-AGP antibody using a solution obtained by desialylating AGP in a sample followed by dilution of the desialylated AGP, and converting the concentration of AGP in the specimen from the color development amount or the emission amount based on an enzyme reaction using a calibration curve.

For example, a calibration curve is preferably prepared from the relationship between the amount of AGP (concentration) and the color development amount or the emission amount (μg/ml) by using a commercially available human plasma AGP (specifically Sigma-Aldrich) (known concentration) as a standard sample, which is desialylated, and performing a sandwich ELISA using an anti-AGP antibody immobilized on a substrate and an enzyme-labeled anti-AGP antibody.

[Process of Normalizing Amount of Fucosyl Residues with AGP Amount]

The measurement method preferably further includes a step of normalizing the amount of fucosyl residues in a specimen obtained above by the amount of AGP (U/μg) obtained in the above-described "Process of Quantifying AGP in Specimen".

In a conventional method, fucose added to an N-linked glycans can be analyzed by the CAIE method or the MALDI-TOF-MS, but the operation is complicated, the results cannot be obtained quickly, and quantification of the amount of fucose is difficult. In contrast, the amount of fucosyl residues per unit amount of AGP in a specimen can be calculated easily and quickly by the present step.

[Diagnostic Criteria for Pancreatic Cancer or Malignant Intraductal Papillary Mucinous Neoplasm (IPMC)]

In the present embodiment, the diagnostic criteria for having pancreatic cancer or IPMC are not particularly restricted, and for example, the following criterion may be used: a diagnostic criterion of having pancreatic cancer or IPMC when the amount of fAGP in a specimen is greater than a reference value or greater than the amount of fAGP in a specimen collected from healthy subjects or IPMA patients; or a diagnostic criterion of having pancreatic cancer or IPMC when the amount of fAGP in a specimen is greater than a reference value or greater than the amount of fAGP in a specimen collected from an IPMA patient.

The reference value may be a cut-off value predetermined based on measurements of healthy subjects and/or IPMA patients by a method known to those skilled in the art, and for example, the cut-off value may be the mean value of the measurement values of healthy subjects (mean)+3× standard deviation (S.D.).

In the present invention, a healthy subject means a person who does not suffer from cancer or a disease with acute inflammation or chronic inflammation.

In the present invention, the diagnosis may be a diagnosis of a treatment prognosis for pancreatic cancer or IPMC.

Examples of pancreatic cancer treatment include one or more selected from the group consisting of surgery, chemotherapy, radiation therapy, antibody therapy, and immunotherapy. The treatment is preferably one or more selected from the group consisting of surgery, chemotherapy, and radiation therapy. Examples of the immunotherapy include an immunotherapy using an antibody drug or a molecularly-targeted drug. Examples of IPMC treatment include surgery.

The diagnosis is not particularly limited, and may be, for example, a determination of no response to treatment or poor prognosis when a specimen taken from a post-treatment patient is measured and determined to have pancreatic cancer or IPMC, according to the criteria described in the above-described section "Diagnostic Criteria for Pancreatic Cancer or Malignant Intraductal Papillary Mucinous Neoplasm (IPMC)".

Another embodiment of the present invention is a kit for diagnosis of pancreatic cancer or IPMC.

The kit is a kit containing the following elements (A) to (C), preferably (A) to (D), or more preferably (A) to (E).

(A) a reagent for desialylation, (B) a substrate for an EIA on which an anti-AGP antibody is immobilized (C) a reagent for defucosylating an anti-AGP antibody immobilized on a substrate for an EIA, and (D) a labeled lectin (for example, AAL) such as biotin-labeled lectin, and (E) an avidin-labeled enzyme (for example, HRP).

The kit preferably further includes (F) a substrate for sandwich ELISA on which an anti-AGP antibody is immobilized for quantifying AGP in a specimen, and (G) a solution containing an enzyme (for example, HRP) labeled anti-AGP antibody.

The kit preferably further includes a buffer solution for dilution, a buffer solution for blocking, and an fAGP standard. As the fAGP standard, for example, a partially purified product from ascites or serum derived from a human cancer patient can be used, or a culture solution of human-derived cultured cells, such as a hepatoma cell line, can be used.

As for preferable types, concentrations, labeling, and conditions for use of the above-described (A), (C) to (E) and (G), the description of the measurement of the amount of fAGP included in the above-described data acquisition method of the present invention is applicable. Each solution may be concentrated as appropriate prior to use, and may be diluted as appropriate with water or the like immediately prior to use.

When any of the above-described (A), (C) to (E) and (G) contain a plurality of solvents or solutions, they may be mixed and contained in a single container or may be contained in separate containers.

Examples of preferable forms of the above-described (B) and (F) include aspects described in the above-described description of the measurement method of the present invention.

The kit is for diagnosis for pancreatic cancer or IPMN, and regarding diagnostic criteria for whether or not a patient suffers from pancreatic cancer or IPMN, the criteria described in the above-described data acquisition method of the present invention can be used.

The kit may further include an instruction manual or the like describing the method of measuring the amount of fAGP included in the above-described data acquisition method of the present invention.

EXAMPLES

The present invention will be described using Examples below, but the present invention is not limited to these Examples.

Example 1

[Comparison of Amount of fAGP in Serum in IPMN Patients, Pancreatic Cancer Patients, and Healthy Subjects]

Using a specific method for measuring fucosyl residues expressed on the AGP molecule already established by the present inventors (Patent Document 1 and Non-Patent Document 6), the amounts of fAGP in preoperative sera from IPMN patients and pancreatic cancer patients and in sera from healthy subjects as negative controls were measured. A very small amount of serum sample was used for each specimen (1 drop, 25 μl). For IPMN patients, classification of IPMC or IPMA was made by postoperative lesion histology, which is a method known to those skilled in the art.

The measurement of the amount of fAGP in a serum was performed by first measuring the amount of AGP in the serum by a sandwich ELISA using an anti-AGP antibody for normalization, then measuring the amount of fAGP in the serum by an EIA using an anti-AGP antibody/fucose-binding lectin (AAL), and calculating the amount of fucosyl residues per unit amount of AGP in a serum from results of these measurements. IPMN patients were divided into IPMC and IPMA and represented separately and compared with pancreatic cancer patients and healthy subjects as negative controls (FIG. 1).

The amount of fAGP in sera of IPMC (n=14) and IPMA (n=7) was significantly higher ($P<0.05$) in IPMC relative to IPMA at 118.15±113.01 and 11.63±8.47 U/μg, respectively. IPMAs were significantly higher for healthy subjects (indicated as Healthy control in the FIGURE, n=53) (4.07±3.49U/μg) (P<0.05), and pancreatic cancer patients (indicated as Ca. Pancreas in the FIGURE, n=40) (904.37±1708.32 U/μg) significantly higher for IPMCs (P<0.05).

The cut-off value (mean±3S.D.=14.54U/μg) was determined from the amount of fAGP measured in healthy subjects, and the positive rate in each specimen group was confirmed. As a result, pancreatic cancer patients: 97.5% (39/40), IPMC patients: 92.86% (13/14), IPMA patients: 28.6% (2/7), and healthy subjects: 1.9% (1/53). Based on this cut-off value, the accuracy of IPMC was determined to be 85.7%, which was markedly higher than the accuracy of conventional imaging (58.8%). The positive rate in pancreatic cancer was extremely high.

Example 2

[Comparison of Preoperative Blood Concentrations of fAGP and Other Cancer Markers of Pancreatic Cancer in IPMN Patients]

The amount of fAGP in sera of respective IPMN patients measured in Example 1 was shown in Table 1. The results of the measurement of four antigens (CEA, CA19-9, SPan-1, and DUPAN-2), which are conventionally utilized as cancer markers of pancreatic cancer by a method known to those skilled in the art, using serum samples derived from the same patients as the samples used in Example 1 are also shown in Table 1.

When the positive rates of CEA, CA19-9, SPan-1, and DUPAN-2, which are conventionally utilized as cancer markers for pancreatic cancer, were examined in the preoperative sera of 14 IPMC cases, all markers of CEA (1/14=7.1%), CA19-9 (5/14=35.7%), SPan-1 (1/14=7.1%), DUPAN-2 (1/14=7.1%), except CA19-9, were low (Table 1).

Here, the antigenic determinant of CA19-9 is sialyl Lea (NANAα2,3Galβ1,3 [Fucα1,4]GlcNAc), which is the common antigenic determinant of human Lewis blood group antigen, $Le^a$ (Galβ1,3 [Fucα1,4]GlcNAc), and both have the same key enzyme involved in Fuca1,4 sugar chain synthesis. In Japan, approximately less than 20% of humans are negative for the Lewis blood groups and cannot synthesize Fuca1,4 linkages, and therefore, sialyl $Le^a$ cannot be genetically synthesized, resulting that CA19-9 cannot be a cancer marker in these cases. The present inventors have already found that typing of the Lewis blood group is difficult by a conventional serological tests and that accurate typing is not possible because cancer-related changes of phenotypes occur frequently (see Non-Patent Document 7). For accurate typing of Lewis blood groups, measurement of FUT6 enzyme activity or FUT6 genotyping is required (see Non-Patent Document 8). In addition to these limitations of CA19-9, the results in Table 1 indicate that the sensitivity of CA19-9 measurement for the diagnosis of IPMC is low, and the superiority of fAGP measurement for IPMN diagnosis and IPMC discrimination is clear.

TABLE 1

Preoperative Blood Concentrations of fAGP and Tumor Markers in IPMN Patients

| | Patient | fAGP (U/μg) | CEA (ng/ml) | CA19-9 (U/ml) | Span-1 (U/ml) | DUPAN-2 (U/ml) |
|---|---|---|---|---|---|---|
| 1 | IPMC | 241.96 | 4.2 | 38 | 23.3 | 25 |
| 2 | IPMC | 72.35 | 2.2 | 6 | 10.0 | 25 |
| 3 | IPMC | 322.84 | 9.0 | 39 | 21.4 | 25 |

TABLE 1-continued

Preoperative Blood Concentrations of fAGP and Tumor Markers in IPMN Patients

| | Patient | fAGP (U/μg) | CEA (ng/ml) | CA19-9 (U/ml) | Span-1 (U/ml) | DUPAN-2 (U/ml) |
|---|---|---|---|---|---|---|
| 4 | IPMC | 7.15 | 2.8 | 28 | 19.4 | 25 |
| 5 | IPMC | 47.41 | 1.3 | 14 | 11.1 | 25 |
| 6 | IPMC | 61.21 | 3.1 | 79 | 55.7 | 263 |
| 7 | IPMC | 224.28 | 3.4 | 22 | 13.4 | 25 |
| 8 | IPMC | 333.53 | 1.1 | 54 | 29.0 | 71 |
| 9 | IPMC | 19.76 | 1.0 | 14 | 13.8 | 25 |
| 10 | IPMC | 69.17 | 3.6 | 22 | 25.0 | 16.9 |
| 11 | IPMC | 30.32 | 1.0 | 54 | 29.7 | 32 |
| 12 | IPMC | 113.76 | 4.0 | 13 | 10.0 | 25 |
| 13 | IPMC | 74.46 | 3.3 | 16 | 15.3 | 25 |
| 14 | IPMC | 35.85 | 1.9 | 8 | 10.0 | 25 |
| 15 | IPMA | 3.05 | 4.0 | 2 | 12.5 | 25 |
| 16 | IPMA | 4.8 | 2.2 | 1 | 25.0 | 10 |
| 17 | IPMA | 3.48 | 2.5 | 1 | 10.0 | 43 |
| 18 | IPMA | 23.43 | 4.1 | 33 | 22 | 25 |
| 19 | IPMA | 21.75 | 1.5 | 10 | 10.5 | 25 |
| 20 | IPMA | 12.02 | 2.1 | 13 | 10.3 | 25 |
| 21 | IPMA | 12.87 | 0.7 | 6 | 10.0 | 25 |
| cut-off value | | 14.54 | 5.0 | 37 | 30.0 | 150 |

Underlined numbers are positive cases (>each cut-off value)

From the above, the serum fAGP values measured using a specific measurement method of fucosyl residues expressed on the AGP molecule which the present inventors have already established, were considerably increased in pancreatic cancer, and IPMC can be distinguished at a higher positive rate than conventional cancer markers in the preoperative diagnosis of IPMN patients in all cases. This indicated the possibility of considerably improving the accuracy of conventional imaging diagnosis of cases suitable for surgery (IPMC) in IPMN patients. Since the incidence of pancreatic cancer is considerably increased in IPMC patients, this method is expected to be applied to the diagnosis of pancreatic cancer development in IPMN patients. Therefore, the fAGP value may be a useful biomarker for malignant neoplasm in IPMN patients.

The invention claimed is:

1. A method for diagnosing and treating a patient having malignant intraductal papillary mucinous neoplasm (IPMC) in intraductal papillary mucinous neoplasm (IPMN), comprising:

a step of collecting a specimen from a patient, wherein the specimen is a plasma or a serum;

a step of measuring the amount of fucosyl residues of $\alpha_1$-acid glycoprotein (AGP) in the specimen, comprising:

a step of desialylating AGP in the specimen;

a step of measuring the amount of AGP in the specimen as μg/ml by a sandwich enzyme-linked immunosorbent assay (ELISA) using an anti-AGP antibody that is immobilized on a substrate, an enzyme-labeled anti-AGP antibody, and desialylated AGP preparations that are used as standards for quantifying AGP;

a step of measuring the amount of fucosyl residues in the specimen as U/ml by an enzyme immunoassay (EIA) using an anti-AGP antibody that is immobilized on a substrate and whose sugar chain has been defucosylated, and a labeled lectin that binds a fucosyl residues in the desialylated AGP; and a step of normalizing the amount of the fucosyl residues in the specimen with the amount of desialylated AGP to obtain the amount of fucosyl residues of AGP in the specimen as U/μg;

a step of diagnosing IPMC by identifying the amount of the fucosyl residues of AGP in the specimen as being greater than a reference value or as being greater than an amount of fucosyl residues of AGP in a specimen collected from a patient with a benign intraductal papillary mucinous neoplasm (IPMA); and a step of treating said patient by one or more selected from the group consisting of surgery, chemotherapy, radiation therapy, antibody therapy, and immunotherapy.

2. The method according to claim 1, wherein the desialylation is performed by a sialidase treatment, and the defucosylation is performed by periodate oxidation.

3. The method according to claim 1, wherein the labeled lectin is labeled *Aleuria aurantia* lectin (AAL).

4. The method according to claim 1, wherein the diagnosis is a diagnosis of a prognosis of a treatment against IPMC.

* * * * *